United States Patent
Rezai et al.

(12) 
(10) Patent No.: US 6,609,030 B1
(45) Date of Patent: Aug. 19, 2003

(54) METHOD OF TREATING PSYCHIATRIC DISEASES BY NEUROMODULATION WITHIN THE DORSOMEDIAL THALAMUS

(75) Inventors: Ali R. Rezai, New York, NY (US); Brian H. Kopell, New York, NY (US)

(73) Assignee: ElectroCore Techniques, LLC, Summit, NJ (US)

( * ) Notice: Subject to any disclaimer, the term of this patent is extended or adjusted under 35 U.S.C. 154(b) by 0 days.

(21) Appl. No.: 09/511,842

(22) Filed: Feb. 24, 2000

(51) Int. Cl.[7] ................................................. A61N 1/18
(52) U.S. Cl. .............................. 607/45; 600/93; 600/508
(58) Field of Search ........................ 607/3, 45; 604/500, 604/502, 506, 93

(56) References Cited

U.S. PATENT DOCUMENTS

| | | | |
|---|---|---|---|
| 5,713,923 A | * 2/1998 | Ward et al. | ..................... 607/3 |
| 6,134,474 A | * 10/2000 | Fischell et al. | ................ 607/45 |
| 6,167,311 A | * 12/2000 | Rezai | ........................... 607/45 |
| 6,227,203 B1 | * 5/2001 | Rise et al. | ................... 128/898 |

* cited by examiner

Primary Examiner—Carl Layno
(74) Attorney, Agent, or Firm—Joseph P. Errico, Esq.; Timothy J. Bortree, Esq.

(57) ABSTRACT

A method for treating psychiatric diseases such as Affective Disorder (including Major Depression and Bipolar Disorder), Anxiety Disorder (including General Anxiety Disorder, Obsessive Compulsive Disorder and Panic Disorder) by stimulation (either electrical and/or chemical) of the thalamus, and in particular a region within the dorsomedial nucleus of the thalamus. The method includes the steps of determining a common group of patients, each suffering from a common specific diagnosis for a psychological disorder; determining which common region of the patients' thalami are involved in carrying the pathological electrical signals and/or metabolic activity which may otherwise be generated in dissimilar and disparate regions of the brains of the patients; surgically implanting an electrode and/or catheter and electrical signal generating device and/or drug pump such that the electrode and/or catheter is positioned within the region of the thalamus identified as the dorsomedial nucleus; and selectively adjusting the level of electrical and/or chemical stimulation in accordance with the specific effect of the stimulation of the patient. In particular, the region of the thalamus most frequently associated with the aforementioned psychiatric disease is the dorsomedial nucleus.

3 Claims, 4 Drawing Sheets

Fig. d) Model of Affective Disorder

METHOD OF TREATING PSYCHIATRIC DISEASES BY NEUROMODULATION WITHIN THE DORSOMEDIAL THALAMUS

BACKGROUND OF THE INVENTION

1. Field of the Invention

This invention relates generally to the treatment of psychiatric disorders by stimulating appropriate regions of the thalamus, and more particularly to a method of modulating pathological electrical and/or chemical activity of the brain by electrical and/or chemical stimulation of the corresponding nucleus or nuclei of the thalamus, and most specifically to the stimulation of the dorsomedial nucleus of the thalamus.

2. Description of the Prior Art

The treatment of psychiatric disorders by neurosurgical techniques has an extensive history. In the early 1930's Fulton and Jacobsen first recognized that an experimentally induced neurotic behavior in chimpanzees could be abolished by frontal lobectomy. Within a few years, Freeman and Watts developed the first psychosurgical procedure for humans known as the frontal lobotomy. As the inherent physiology of the frontal lobe became more evident, the original freehand procedure of Freeman and Watts became less and less extensive. By the late 1940's, the method of stereotaxis, in which the patient's brain is modeled in 3-dimensional space for exquisite targeting accuracy, merged with lesioning techniques resulting in an even more efficacious and safe psychosurgical procedure. Further developments of stereotactic equipment have combined with novel advancements in functional and anatomic imaging to encompass the state of the art in the neurosurgical treatment of psychiatric disorders today. However, the fundamental limitation of these lesioning techniques is that they are inherently irreversible and static in nature. There is no proverbial "off" switch to alleviate side effects and no way to adjust the desirable effects in response to a patient's changing symptom profile.

Within the field of neurosurgery, the use of electrical stimulation for treating pathologies, including such disorders as compulsive eating, chronic pain, and movement disorders, such as Parkinson's disease essential tremor, has been widely discussed in the literature. It has been recognized that electrical stimulation holds significant advantages over alternative methods of treatment, for example lesioning, inasmuch as lesioning can only destroy nerve activity. In many instances, the preferred effect is to stimulate or reversibly block nervous tissue. Electrical stimulation permits such stimulation of the target neural structures, and equally importantly, it does not require the destruction of the nervous tissue (it is a reversible process, which can literally be shut off or removed at will).

Another technique which offers the ability to affect neuronal function in a reversible and dynamic fashion is the delivery of drugs directly to target tissues via a subcutaneously implanted pump. Such drugs, either traditional psychiatric agents or chemicals mimicking neurotransmitters, could be instilled at such low doses as to completely avoid the side effects so common to moden pharmacotherapy. Such doses could also be tailored in magnitutde with regard to a particular patient's varying symptomatology. A chemical neuromodulating system could be implanted as a primary treatment strategy or in combination with an electrically based one. A combination therapeutic approach, one combining electrical and chemical means, would be penultimate to regenerating healthy neuronal tissue.

Within this field, however, disorders manifesting gross physical dysfunction, not otherwise determinable as having emotional or psychiatric origins, comprise the vast majority of those pathologies treated by deep brain stimulation. A noteworthy example of treatment of a gross physical disorder by electrical stimulation is included in the work of Alim Benabid, and his research team, who have proposed a method of reducing, and in some cases eliminating, the temor associated with Parkinson's disease by the application of a high frequency electrical pulse directly to the subthalamic nucleus (see Neurosurgical Operative Atlas, Vol. 8, March 1999, pp. 195–207, Chronic Subthalamic Nucleus Stimulation For Parkinson's Disease; and New England Journal of Medicine, Vol. 339, October 1998, pp. 105–1111, Electrical Stimulation of the Subthalamic Nucleus in Advanced Parkinson's Disease).

Conversely, direct neuroaugmentation treatments for disorders which have traditionally been treated by behavioral therapy or psychiatric drugs, has been largely limited to the stereotactic lesioning procedures mentioned above. The are four lesioning techniques mostly in use today: cingulotomy, capsulotomy, subcaudate tractotomy, and limbic leucotomy. Such procedures have been applied to date in the treatment of Affective disorders and Anxiety disorders. If one critically examines the results of these procedures in the literature, it would be apparent, when applied to a carefully selected patient population in conjuction with modern equipment and imaging techniques, these procedures are both efficacious and safe. In fact, in a certain subset of patients who have failed all conventional (pharmacotherapy and psychotherapy) treatments, these neurosurgical procedures are the only efficacious options available. If would follow that electrical and/or chemical neuromodulating techniques with their inherent reversibility and adjustability would an even better solution than the traditional lesioning techniques. To date, however, intracranial neuromodulation techniques have been largely unexplored. Only recently, in the Oct. 30, 1999 issue of Lancet, have Meyerson et al. described a technique for deep brain electrical stimulation of the anterior internal capsule for OCD patients. While the results are preliminary, they are also quite promising as three of the four patients had good results.

Another effort has been made to treat psychiatric disorders via peripheral nerve stimulation. A noteworthy example is the effort to control compulsive eating disorders by stimulation of the vagus nerve which has been described by Wernicke, et al. in U.S. Pat. No. 5,263,480. This treatment seeks to induce a satiety effect by stimulating the afferent vagal fibers of the stomach. For patients having weak emotional and/or psychological components to their eating disorders, this treament can be effective insofar as it eliminates the additional (quasi-normal) physio-chemical stimulus to continue eating. This is especially true for patients who exhibit subnormal independent functioning of these fibers of the vagus nerve. For compulsive eating patients who are not suffering from an insufficient level of afferent vagal nerve activity resulting from sufficient food intake, however, the over stimulation of the vagus nerve and potential resultant over abundance of satiety mediating chemicals (cholecystokinin and pancreatic glucagon) may have little effect It has even been suggested that continued compulsive eating, despite overstimulation of the vagus nerve, may exacerbate the emotional component of the patient's disorder. This, therefore, begs the question, is vagus nerve stimulation useful in treating the psychological component of the disorder of compulsive eating, or is it simply a method of minimizing the additional, but natural, pressures to eat because of normal physical hunger. More generally, the question may be asked, is peripheral nerve stimulation of any kind the most appropriate method of treatment for disorders which are, at the core, the result of a pathology exhibited in the brain.

If the answer to this question is that the stimulation of a peripheral nerve can result in the release of a chemical which specifically counteracts the psychological pathology, for example if the release of greater amounts of cholecystokinin and pancreatic glucagon had a direct effect on the pathology exhibited in the brain, then, for that patient, the treatment will have a greater probability of success. If, however, as is most probably the case, the increase in the level of activity of the peripheral nerve does not result in the release of such a chemical, and therefore, has no effect on the area of the brain responsible for the emotional/psychiatric component of the disorder, then the treatment will have a much lower probability of success.

The impetus, therefore, would be to treat psychiatric disorders with direct modulation of activity in that portion of the brain causing the pathological behavior Unfortunately, the ability to determine what region of the brain is responsible for a given patient's disorder is very difficult, and even more importantly, does not usually provide consistent patterns across a population of similarly afflicted patients. By this it is meant that the region of the brain which causes the behavioral pathology of one compulsively eating patient, for example, does not necessarily correspond in any way with the region of another compulsively eating patient.

In some manner, however, the determination of what regions of the brain are exhibiting pathological function must be determined. Fortunately, a method for determining precisely this has been developed by a number of researchers. Normal brain function can be characterized by four discrete frequencies of electrical output. Other frequencies are almost exclusively associated with pathology. The use of magnetoencephalography (MEG scans) has permitted quantificaion of electrical activity in specific regions of the brain. It has been proposed that MEG scans may be used to identify regions exhibiting pathological electrical activity. The resolution of the MEG scans of the brain are highly accurate (sub-one millimeter accuracy), however, correlating the MEG scan with MRI images for the surgical purposes of identifying anatomical structures limits the overall resolution for surgical purposes to a volume of 10 to 30 cubic millimeters. As stated above, however, simply identifying the regions of the brain which are exhibiting pathological electrical activity for a specific patient is not sufficient to generalize across a large population of patients, even if they are exhibiting identical disorders.

Fortunately, the architecture of the brain provides a substantial advantage in the search for a generic solution. This design advantage takes the form of a centralized signalling nexus through which many of the brain's disparate functions are channeled in an organized and predictable manner. More particularly, the thalamus is comprised of a large plurality (as many as one hundred, or more) of nerve bundles, or nuclei, which receives and channels nerve activity from all areas of the nervous system and interconnects various activities within the brain. The thalamus has been metaphorically described by some as the brain's equivalent of a highly organized train station. Many different train tracks come together, and many trains carrying many different cargos enter, however, if one has a schedule and a map, it is easy to find all the trains which carry coal (whether from Pennsylvania, West Virginia, Tennessee, or Arkansas), because all coal carriers are routed through the same tracks.

It is this key which permits the treatment of common psychiatric disorders by brain stimulation of one specific area, rather than having to customize the (gross) placement of the stimulator and/or catheter for each patient.

It is therefore the principal object of the present invention to provide a more generically applicable method for treating certain psychiatric disorders.

It is further an object of the present invention to provide a fully reversible and adjustable method of treating certain psychiatric disorders.

It is still further an object of the present invention to provide a method of treating certain psychiatric disorders the effectiveness of which may be evaluated rapidly.

It is also an object of the present invention to provide a method of interventionally treating certain psychiatric disorders while minimizing the necessary pathological investigation.

SUMMARY OF THE INVENTION

The preceding objects are provided in the present invention, which comprises new and novel methods of treating psychiatric disorders by implantation of stimulation lectrodes and/or drug-delivery catheters at a specific location in the thalamus. In another aspect, the present invention also comprises new and novel methods for identifying the proper positioning of the electrodes and/or catheters within the thalamus for a given specific psychiatric disorder. More particularly, in the first aspect, the present invention comprises a method of therapeutically treating a psychiatric disorder by surgically implanting an electrode and/or drug-delivery catheter into a predetermined site within the brain of the patient, wherein the predetermined site is selected from within the dorsomedial thalamus. Referring more particularly to FIG. 1, the dorsomedial nucleus 101 is located dorsal to the medial thalamic nucleus 102 and medial to the, intralaminal nucleii 103. The dorsomedial thalamic nucleus is coupled most directly to the orbitofrontal cerebral cortex which is most associated with personality and behavior. The OFC is particularly implicated in the pathogenesis of various psychiatric diseases. There are two main loops connecting the dorsomedial nucleus and the OFC. A direct, reciprocally excitatory loop is mediated by the neurotransmitter glutamate. An indirect, modulatory loop occurs via connections through the ventromedial striatum and glocus pallidus, and is thought to be mediated by multiple neurotransmitters including: GABA, dopamine, and serotonin. The dorsomedial nucleus also has connections to the limbic system. The limibc system is a group of structures in the brain which are thought to mediate the emotional state. At the core of this system is the Papez circuit, first illustrated in 1937, which includes the cingulate gyrus, the anterior thalamic nucleus, the amygdala, the fornix, and the mamillary bodies. The dorsomedial thalamic nucleus has been shown to have connections with the basolateral amygdala.

In the first aspect of the invention, therefore, the proximal end of the electrode and/or catheter is coupled to an electrical signal source and/or drug delivery pump which, in turn, is operated to stimulate the predetermined treatment site in the orbitofrontal cortex of the brain, such that the clinical effects of the psychiatric disorder are reduced.

In the second aspect, the present invention comprises a method of determining the proper therapeutic treatment, i.e., the proper position or placement of the electrodes, for a specific psychological disorder comprising the steps of identifying a large sampling of patients, each exhibiting a common specific psychological disorder and then identifying which common region or nuclei of their thalamuses exhibits pathological electrical activity during manifestations of the specific psychological disorder. The common regions demonstrating this pathological activity constitute the predetermined treatment site, whereafter a suitable means for affecting the activity of said predetermined treatment site may be employed to ameliorate the psychological disorder generically with a high probability of success.

In particular, the region identified above, the dorsomedial thalamic nucleus is herein identified by its known anatomical connections and functional brain imaging as being actively involved in channeling or gating the pathological electrical and/or metabolic activity associated with psychiatric disorders. It is important to note that this region, its functions, and its connections are common structural features of human brains, and therefore is a common target across a large number of patients. As suggested above, this commonality of function and structure within the thalamus allows for common treatment targeting, even in instances wherein different patients have other disparate locations within their brains that also exhibit pathological electrical and/or metabolic activity.

DETAILED DESCRIPTION OF THE PREFERRED EMBODIMENT

Figure 1:
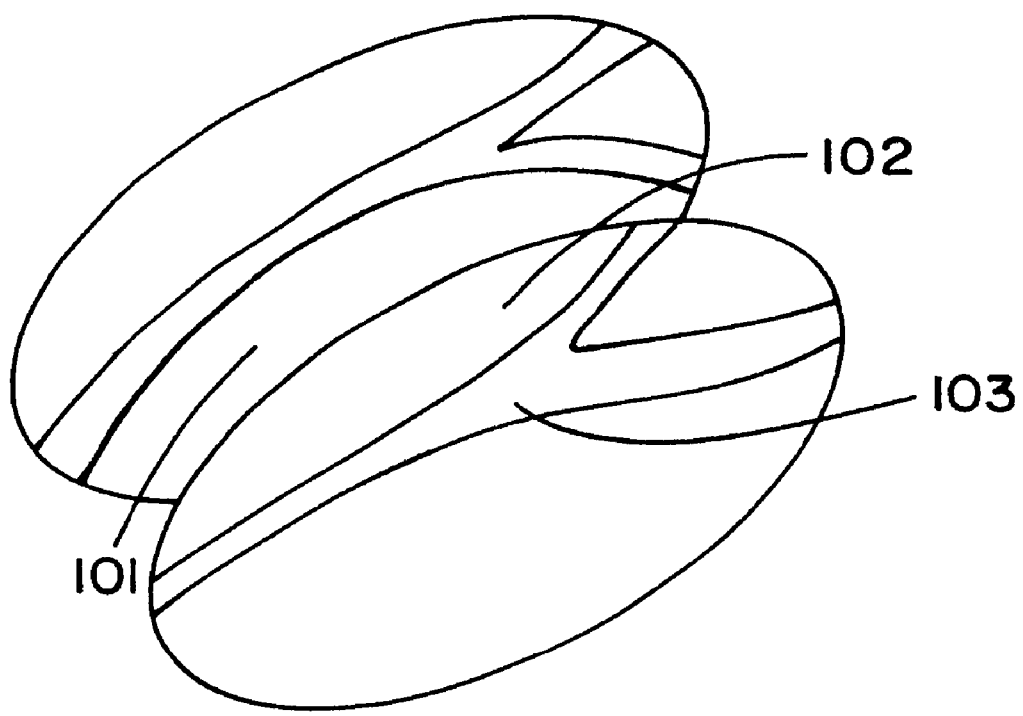
FIG. 1 is a perspective view of a human thalamus, having various regions thereof outlined.
Figure 2:
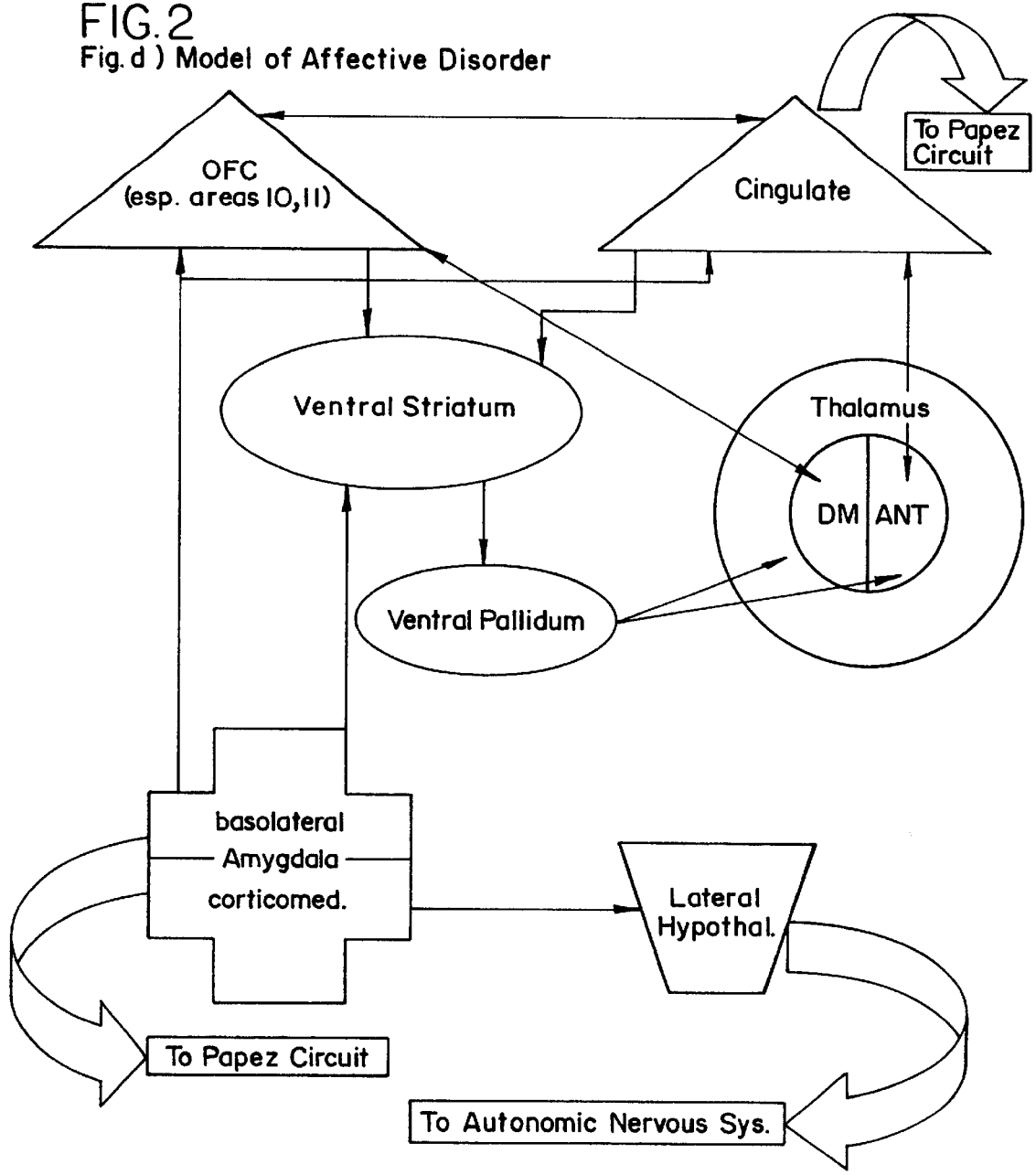
FIG. 2 is a conceptual circuit diagram illustrating the coupling of relevant regions of the human brain which are involved in psychological disorders.

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

The present invention comprises a method of identifying and treating patients who suffer from certain known psychological disorders. As suggested by this introductory statement, the specific steps involved with this method comprise two separate stages: first, the identification of patients and the preparation for surgical intervention; and second, the actual surgical procedure.

With respect to the first of these stages, that is the pre-operative steps, the identification of suitable patients begins with the accumulation of physical, chemical, and historical behavioral data on each patient. A collection of patients who have been identified as exhibiting similar clinical symptoms are then grouped together and subject to a series of common non-invasive brain imaging studies.

These brain imaging studies are intended to identify the regions of the brain, and more particularly, the regions of the thalamus, which exhibit clinically recognizable deviation from normal electrical activity. Several diagnostic tools are useful in this capacity, including fluoro-deoxyglucose-positron-emission tomography (FDG-PET), electroencephalography (EEG), magpetic resonance imaging (MRI), and most importantly, magnetoencephelagraphy.

A magnetoencephalograph (MEG) is a device which utilizes a plurality of spatially distributed, highly sensitive, superconducting circuits to register the electrical activity of the brain. The circuits can measure the frequency of the activity at different points in the brain by correlating the interferences registered in each superconducting circuit. As the normal frequencies of brain activity are known, and specific frequency ranges associated with neural dysfunction have been reported, it is possible to identify the specific regions of the brain exhibiting neural dysfunction.

The correlation of specific areas of the brain which are not demonstrating normal activity across a group of patients exhibiting similar clinical symptoms and who are similarly diagnosed is not assumed a priori. The nature of the brain's architecture provides a substantial advantage in this arena. The brain channels nearly all of its signalling activity through the thalamus. In an organized fashion, similar peripheral activity, i.e. activity in the peripheral areas of the brain which are associated with the same, or similar conditions, are channeled through the same areas of the thalamus. In this way, the thalamus acts as a train switching station, or as a post office, rerouting disparate signals along similar paths when the appropriate outcomes of the original signals are similar. This effect is nowhere more impresive than in the examples presently being illustrated. For example, two patients exhibiting similar clinical conditions, for example physical motion tics associated with florid Tourette's syndrome, may have very different peripheral brain dysfunction, but probably channel the abnormal electrical signals through the same nucleus within the thalamus.

The precise mapping of this abnormal signalling, however, is not possible solely by using the MEG. While the use of the MEG is a substantial advantage in determining whether disparate abnormal peripheral activity is channeled through the thalamus in a similar way, the resolution of the device does not permit pinpoint accuracy in this determination. In fact, the resolution of the MEG is substantially less sharp than the implantable electrodes which are to be used in the surgical intervention. The correlation of actual data from test implantations as well as a deep understanding of the brain's architecture is necessary to identify the specific target nuclei. Additionally, however, the instruments utilized in guiding the surgeon in placing the actual electrodes into the thalamus have a similar degree of variability, or limit of resolution. Fortunately, the state of the art in surgical intervention and the resilience of the brain tissue permits a small degree of manipulation of the electrode once it is inserted. In fact, a number of advanced electrode designs have been presented which permit the micromanipulation of each of the electrical contacts' position without macromanipulation of the overall electrode.

In the present invention, psychiatric disorders such as Affective Disorder including Major Depression and Bipolar Disorder), Anxiety Disorder (including General Anxiety Disorder, Obsessive-Conmpulsive Disorder, and Panic Disorder) and Substance Abuse Disorder are identified as having a probable commonality in thalamic activity associated with the dorsomedial nucleus. Therefore, once a patient has been identified as exhibiting abnormal clinical behavior symptomatic of one of these disorders, subsequent preoperative brain imaging scans are used to support the presumption that the abnormal signals associated with the disorder are being channelled through one of these related regions of the thalamus, and then surgical intervention with electrical and/or chemical stimulation is taken.

Figure 3:
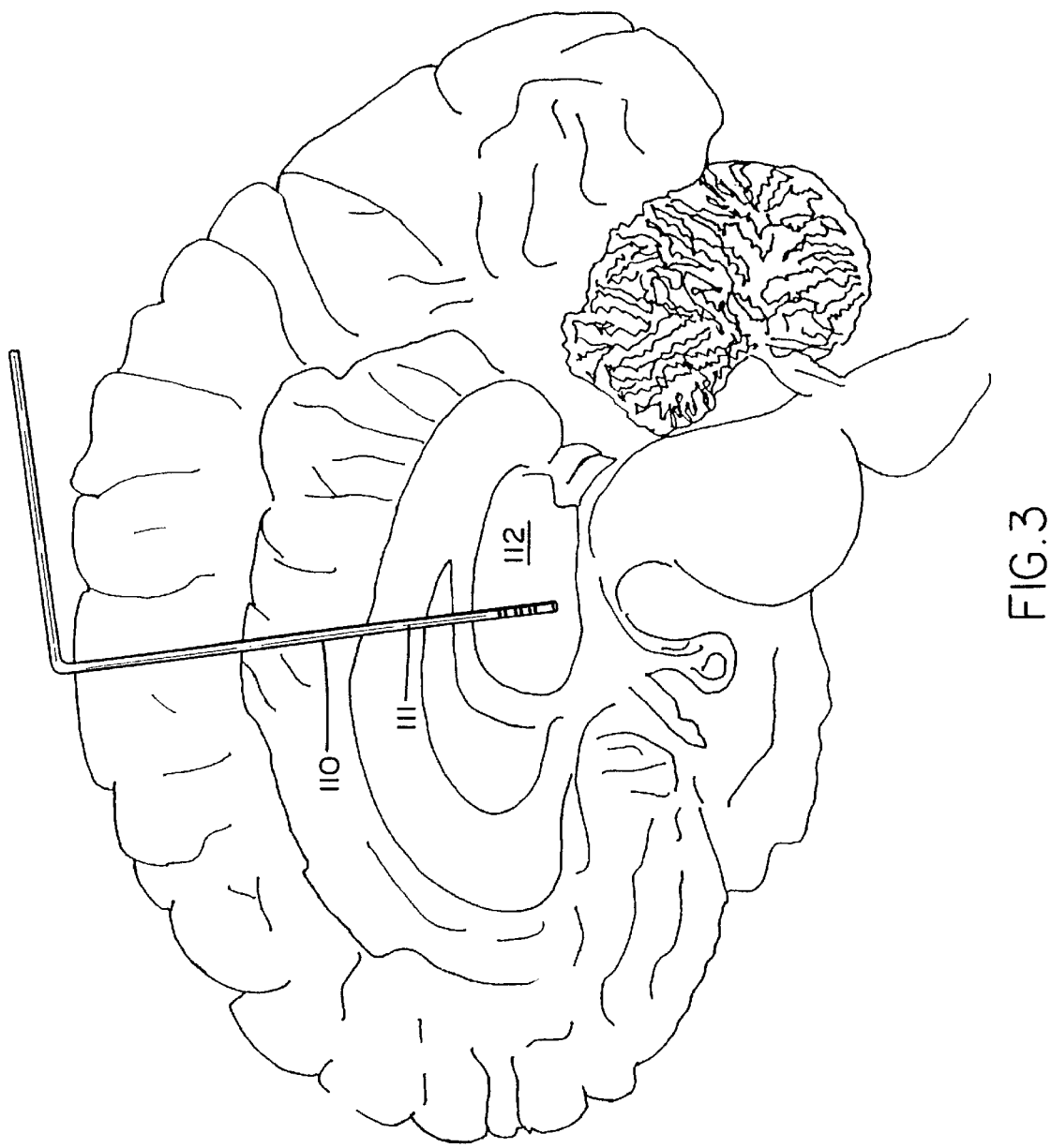
FIG. 3 is a side cross-section view of a human brain having a stimulation electrode implanted in the thalamus in acordance with a method which is an aspect of the present invention.
Figure 4:
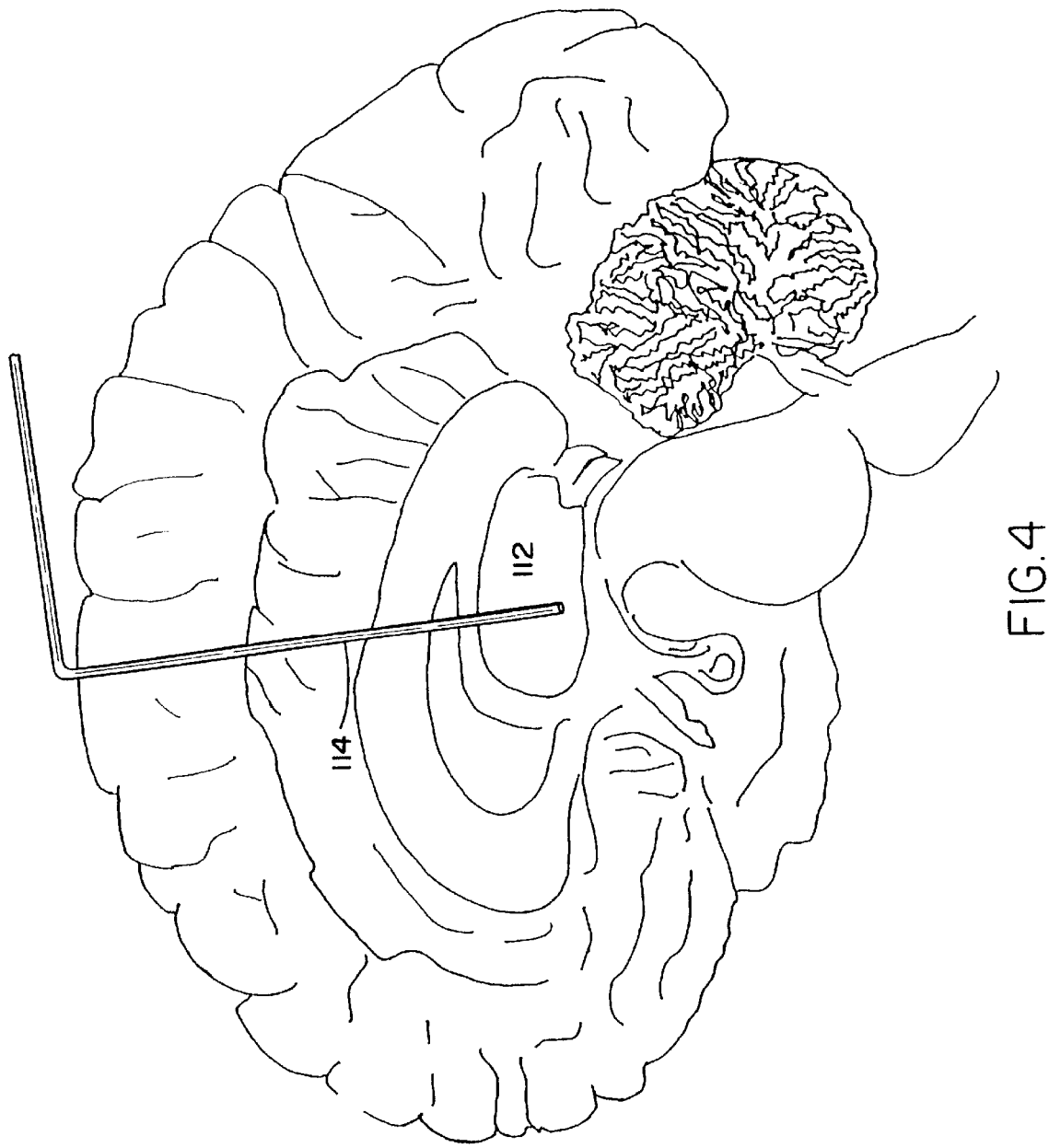
FIG. 4 is a side cross -section view of a human brain having a drug-delivery catheter implanted within the thalamus in accordance with as method which is an aspect of the present invention.

Surgical intervention comprises the second stage of the treatment. It is the specific use of the stimulator and/or drug-delivery system, for treatment of psychiatric disorders which comprises the inventive step in the present method, and not the implantation technique itself. More particularly, the standard neurosurgical techniques for implantation of an electrical stimulation device and/or drug delivery catheter into the brain may be utilized. In fact, referring to FIGS. 3 and 4, in which a side cross-section of a human brain 110 having a stimulation electrode 111/catheter 114 implanted into the thalamus 112 (and more particularly, the dorsomedial nucleus thereof) is provided, it shall be understood that the impantation of electrodes and/or cathteters into various regions of the brain, including the thalamus is known. It is the application of this technique for the treatment of psychiatric disorders which has not previously been described. This technique, therefore, is as follows.

Patients who are to have an electrode implanted into the brain, first have a steroetactic head frame, such as the Leksell, CRW, or Compass, is mounted to the patient's skull by fixed screws. Subsequent to the mounting of the frame, the patient undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The head frame is therefore rigidly mounted to the sugical table. Subsequently, a series of reference points are established relative aspects of the frame and patient's skull, so that the computer can adjust and calculate the correlation between the real world of the patient's head and the virtual space model of the patient MRI scans. The surgeon is able to target any region within the stereotactic space of the brain within 1 millimeter precision. Initial anatomical target localization is achieved either directly using the MRI images, or indirectly using interactive anatomical atlas programs which map the atlas image onto the steroetactic image of the brain. In the present invention, the target space is that occupied by the anterior and intralaminar nuclei.

The surgery itself can be performed under either local or general anaesthetic. An initial incision is made in the scalp, preferably 2.5 centimeters lateral to the midline of the skull anterior to the coronal suture. A burr hole is then drilled in the skull itself; the size of the hole being suitable to permit surgical manipulation and implantation of the electrode. This size of the hole is generally about 14 millimeters. The dura is then opened, and a fibrin glue is applied to minimize cerebral spinal fluid leaks and the entry of air into the cranial cavity. A guide tube cannula with a blunt tip is then inserted into the brain parechyma to a point approximately one centimeter from the target tissue. At this time physiological localization starts with the ultimate aim of correlating the anatomical and physiological findings to establish the final stereotactic target structure.

Physiological localization using single-cell microelectrode recording is preferable for definitive target determination. Sole reliance on anatomical localization can be problematic because of the possible discrepancies between the expected location (expected from the visualization provided by the virtual imaging of the MRI) and the actual position within the skull. Microelectrode recording povides exquisite physiological identification of neuronal firing patterns via direct measures of individual single unit neuronal acitivity. Single-cell microelectrode recordings obtained from intralaminar thalamic cells typically have a characteristic bursting activity. In addition to microelectrode recording, microstimulation and or macrostimulation may be performed to provide further physiological localization.

Once the final target nucleus has been identified in the real spatial frame of reference, the permanent electrode and/or catheter is implanted. General principles guiding the final implantation of an electrode involve the placement of the electrode in a region, and in an orientation, allowing for maximal efficacy while minimizing the undesired side effects. The currently used brain stimulating electrodes are quadripolar electrodes. The electrode itself is approximately 1–1.5 millimeter diameter flexible elastomeric sheath which contains four wound wire leads. The leads terminate at the distal and proximal ends of the sheath in four electrically insulated cylindrical contact pad. The contact pads at the distal end are less than 2 millimeters in length and are separated by an insulating distance, for example between 0.5 and 2 millimeters. At the proximal end, which is anywhere from 25 to 50 centimeters distance from the distal end, a corresponding series of contacts are provided so that the electrode may be coupled to a potential source, or to a coupling lead which permits remote disposition of the signal source.

The drug delivery cathter is a silastic tube similar to the one used in the intrathecal drug delivery systems commonly in use. With regard to catheter placement, care is taken not to place the catheter directly within a vascular structure. This can be achieved by combing data from conventional and/or magnetic resonance angiography into the stereotactic targeting model. The distal portion of the cathter has multiple orifices to maximize delivery of the agent while minimizing mechanical occlusion. The proximal portion of the catheter can be connected directly to a pump or via a metal and/or plastic hollow connector, to an extending catheter.

The initial application of the electrical signal through the electrode is then attempted. The range of signal types are between 0.1 to 20 volts, with a pulse width of 10 microseconds to 1000 microseconds, and a frequency of 2 to 2500 Hertz. The stimulation can be monopolar or bipolar depending upon the specific relative potentials applied to the electrical contacts relative to the patient's tissue. Various stimulation parameters are tested to assess side effects (such as motor contraction, paresthesias, visual disturbance, pain, and autonomic modulation) or clinical efficacy. With regard to a chemical based system, the drug-delivery pump may be programmed with an initial nominal dose scheme. Psychiatric disorders treated by electrostimulation and/or pharmacotherapy, however, may take up to six months to demonstrate clinical efficacy. Long term adjustment of the signal and/or dosage being applied by the power source and/or drug-delivery pump may be required to optimize the outcome. If the patient's symptoms do not subside, the surgeon will attempt to adjust all of the parameters until they do.

As is readily obvious to anyone who has witnessed the unnecessary surgical procedure associated with the remote localization of a power sourceor subcutaneous drug pump, it is desirable the burr cap structure itself comprise the signal and/or drug source. However, as that option is not presently available the signal source generator must be disposed at a remote site in the patient's body. A specially designed plastic cap is generally provided to seat in the burr hole, and permit the proximal end of the electrode to pass out through the skull. The incision in the patient's skull is then sutured closed with the electrode and/or catheter temporarily stored under the skin. If the patient is not already under general anaesthesia, the patient is so disposed and a tunnel is formed under the dermal layers, connecting the incision in the scalp to the remote location for the signal generator (usually the infraclavicular region, beneath the collar bone—where cardiovascular pace makers are implanted). Subsequent joining of the electrode to a coupling (extending) lead from the signal source to the brain electrode is then necessary, however, generally the manner in which the electrode and the lead are coupled utilizes the same terminal contacts as would be used for direct coupling to the power source.

Once the sugery is complete, a non-contrast CT scan is taken to ensure that there is no intracranial hematoma. Subsequently, various stimulation parameters are programmed and patients are assessed for any side effects as well as clinical efficacy. As behavioral and related cognitive improvement may not occur immediately, long-term benefits may not be achieved until multiple adjustmnts are accomplished.

While there has been described and illustrated specific embodiments of new and novel methods of treatment for psychological disorders, it will be apparent to those skilled in the art that variations and modifications are possible without deviating from the broad spirit and principle of the present invention which shall be limited solely by the scope of the claims appended hereto.

We claim:

1. A method of determining the proper therapeutic treatment for, and subsequently treating a specific psychiatric disorder comprising the steps of:

identifying a large sampling of patients, each exhibiting a common specific psychiatric disorder;

identifying which common region of the thalamus exhibits pathological electrical during manifestations of the specific psychiatric disorder, said common region thereafter constituting a predetermined treatment site;

surgically implanting a catheter in the brain of each of said patients so that a distal end thereof lies in communication with the predetermined treatment site in the thalamus of the brain;

coupling a proximal end of said catheter to a fluid medicine delivery pump; and operating said fluid medicine delivery pump to stimulate said predetermined treatment site in the thalamus of the brain, whereby the effects of psychiatric disorder are reduced.

2. The method as set forth in claim 1, wherein said psychiatric disorder is selected from the group consisting of Anxiety Disorder, Affective Disorder, and Substance Abuse Disorder.

3. The method as set forth in claim 1, wherein the common regions of the thalamus constituting the predetermined treatment site is the dorsomedial thalamus.

* * * * *